United States Patent
Anderson et al.

(10) Patent No.: US 11,925,356 B2
(45) Date of Patent: *Mar. 12, 2024

(54) OCCLUSIVE DEVICE WITH EXPANDABLE MEMBER

(71) Applicant: BOSTON SCIENTIFIC SCIMED, INC., Maple Grove, MN (US)

(72) Inventors: James M. Anderson, Corcoran, MN (US); John M. Edgell, Plymouth, MN (US); Jose A. Meregotte, Blaine, MN (US); Steven R. Larsen, Lino Lakes, MN (US); David Raab, Roseville, MN (US); Peter John Hoffman, Brooklyn Center, MN (US); David John Onushko, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 293 days.

This patent is subject to a terminal disclaimer.

(21) Appl. No.: 17/173,549

(22) Filed: Feb. 11, 2021

(65) Prior Publication Data

US 2021/0169491 A1 Jun. 10, 2021

Related U.S. Application Data

(63) Continuation of application No. 16/223,731, filed on Dec. 18, 2018, now Pat. No. 10,952,741.

(Continued)

(51) Int. Cl.
*A61B 17/12* (2006.01)
*A61B 17/00* (2006.01)

(52) U.S. Cl.
CPC ...... *A61B 17/1214* (2013.01); *A61B 17/0057* (2013.01); *A61B 17/12031* (2013.01);
(Continued)

(58) Field of Classification Search
CPC .......... A61B 17/1214; A61B 17/12136; A61B 17/0057; A61B 17/12122;
(Continued)

(56) References Cited

U.S. PATENT DOCUMENTS 1,782,830 A 6/1876 French
1,967,318 A 10/1931 Monahan
(Continued)

FOREIGN PATENT DOCUMENTS

CN 106859722 A 6/2017
WO 9313712 A1 7/1993
(Continued)

OTHER PUBLICATIONS

PCT Search Report from co-pending Application PCT/US02/33808 dated May 20, 2003.
(Continued)

*Primary Examiner* — Julian W Woo
(74) *Attorney, Agent, or Firm* — Seager, Tufte & Wickhem LLP

(57) ABSTRACT

An example medical device for occluding the left atrial appendage includes an expandable member having a first end region, a second end region and an inflation cavity. The medical device also includes a plurality of spine members coupled to the expandable member, the plurality of spine members spaced circumferentially around an outer surface of the expandable member. Additionally, the medical device includes a valve member extending at least partially into the inflation cavity, wherein the plurality of spine members are configured to position the medical device within an opening of the left atrial appendage and wherein the expandable member is configured to expand and seal the opening of the left atrial appendage.

9 Claims, 14 Drawing Sheets

Related U.S. Application Data

(60) Provisional application No. 62/607,053, filed on Dec. 18, 2017.

(52) U.S. Cl.
CPC .. *A61B 17/12122* (2013.01); *A61B 17/12136* (2013.01); *A61B 2017/00243* (2013.01); *A61B 2017/12054* (2013.01); *A61B 17/12172* (2013.01)

(58) Field of Classification Search
CPC .... A61B 17/12031; A61B 2017/12054; A61B 2017/00243; A61B 17/12172
See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |

(56) References Cited

U.S. PATENT DOCUMENTS

| | | |
|---|---|---|
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,096,053 A | 8/2000 | Bates |
| 6,110,243 A | 8/2000 | Wnenchak et al. |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,251,122 B1 | 6/2001 | Tsukernik |
| 6,258,115 B1 | 7/2001 | Dubrul |
| 6,270,490 B1 | 8/2001 | Hahnen |
| 6,277,138 B1 | 8/2001 | Levinson et al. |
| 6,290,674 B1 | 9/2001 | Roue et al. |
| 6,319,251 B1 | 11/2001 | Tu et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,364,895 B1 | 4/2002 | Greenhalgh |
| 6,368,338 B1 | 4/2002 | Knya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,511,496 B1 | 1/2003 | Huter et al. |
| 6,517,573 B1 | 2/2003 | Pollock et al. |
| 6,547,760 B1 | 4/2003 | Samson et al. |
| 6,551,303 B1 | 4/2003 | Van Tassel et al. |
| 6,551,344 B2 | 4/2003 | Thill |
| 6,558,405 B1 | 5/2003 | McInnes |
| 6,562,058 B2 | 5/2003 | Seguin et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,730,108 B2 | 5/2004 | Van Tassel et al. |
| 6,837,901 B2 | 1/2005 | Rabkin et al. |
| 6,855,153 B2 | 2/2005 | Saadat |
| 6,949,113 B2 | 9/2005 | Van Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | van der Burg et al. |
| 7,152,605 B2 | 12/2006 | Khairkhahan et al. |
| 8,197,527 B2 | 6/2012 | Borillo et al. |
| 8,764,793 B2 | 7/2014 | Lee |
| 8,784,469 B2 | 7/2014 | Kassab |
| 9,943,315 B2 | 4/2018 | Kaplan et al. |
| 10,076,335 B2 | 9/2018 | Zaver et al. |
| 10,405,866 B2 * | 9/2019 | Chakraborty .... A61B 17/12122 |
| 10,603,020 B2 | 3/2020 | Rudman et al. |
| 10,952,741 B2 * | 3/2021 | Anderson ........ A61B 17/12031 |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0138094 A1 | 9/2002 | Borillo et al. |
| 2002/0138097 A1 | 9/2002 | Ostrovsky et al. |
| 2003/0023266 A1 | 1/2003 | Borillo et al. |
| 2003/0057156 A1 | 3/2003 | Peterson et al. |
| 2003/0181942 A1 | 9/2003 | Sutton et al. |
| 2003/0220667 A1 | 11/2003 | van der Burg et al. |
| 2004/0098031 A1 | 5/2004 | van der Burg et al. |
| 2004/0215230 A1 | 10/2004 | Frazier et al. |
| 2005/0004652 A1 | 1/2005 | van der Burg et al. |
| 2005/0113861 A1 | 5/2005 | Corcoran et al. |
| 2005/0203568 A1 | 9/2005 | Burg et al. |
| 2015/0005811 A1 | 1/2015 | Lubock |
| 2017/0042550 A1 | 2/2017 | Chakraborty et al. |
| 2019/0069901 A1 * | 3/2019 | Forbes ............. A61B 17/12172 |

FOREIGN PATENT DOCUMENTS

| | | |
|---|---|---|
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |
| WO | 03032818 A2 | 4/2003 |
| WO | 2018187732 A1 | 10/2018 |

OTHER PUBLICATIONS

PCT Search Report from PCT/US99/26325 dated Feb. 15, 2000.

Cragg et al; "Nonsurgical Placement of Arterial Endoprosthesis: A

(56) References Cited

OTHER PUBLICATIONS

New Technique Using Nitinol Wire," Radiology vol. 147, No. 1 pp. 261-263, Apr. 1983.
Cragg et al; "A New Percutaneous Vena Cava Filter", ALJ, 141: 601-604, Sep. 1983.
Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruttenberg, Nonsurgical Therapy of Cardiac Disorders, Pediatric Consult, vol. 5, No. 2, pages not numbered, 1986.
Rashkind et al; "Nonsurgical Closure of Patent Ductus Arteriosus: Clinical Application of the Rashkind PDA Occluder System," Circulation 75, No. 3, 583-592-1987.
Lock et al; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Invite to Pay Additional Fees dated Feb. 22, 2019 for International Application No. PCT/US2018/066163.

\* cited by examiner

OCCLUSIVE DEVICE WITH EXPANDABLE MEMBER

CROSS-REFERENCE TO RELATED APPLICATIONS

This application claims priority to U.S. application Ser. No. 16/223,731, filed Dec. 18, 2018, now U.S. Pat. No. 10,952,741, which claims the benefit of priority under 35 U.S.C. § 119 to U.S. Provisional Application Ser. No. 62/607,053, filed Dec. 18, 2017, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

This disclosure provides design, material, manufacturing method, and use alternatives for medical devices. An example medical device for occluding the left atrial appendage includes an expandable member having a first end region, a second end region and an inflation cavity. The medical device also includes a plurality of spine members coupled to the expandable member, the plurality of spine members spaced circumferentially around an outer surface of the expandable member. Additionally, the medical device includes a valve member extending at least partially into the inflation cavity, wherein the plurality of spine members are configured to position the medical device within an opening of the left atrial appendage and wherein the expandable member is configured to expand and seal the opening of the left atrial appendage.

Alternatively or additionally to any of the embodiments above, wherein each of the spine members extends along a longitudinal axis of the medical device from the first end region to the second end region.

Alternatively or additionally to any of the embodiments above, wherein the second end region includes a bottom surface and wherein at least a portion of each of the spine members is positioned along the bottom surface.

Alternatively or additionally to any of the embodiments above, wherein the expandable member includes a curved portion extending radially inward toward the longitudinal axis, and wherein the curved portion is configured to nest with the opening of the left atrial appendage.

Alternatively or additionally to any of the embodiments above, wherein each of the spine members is positioned along an outer surface of the expandable member.

Alternatively or additionally to any of the embodiments above, wherein a portion of each of the spine members extends into the wall of the expandable member.

Alternatively or additionally to any of the embodiments above, wherein the first end region of the expandable member extends toward a longitudinal axis of the medical device to form an apex.

Alternatively or additionally to any of the embodiments above, wherein the second end region includes a coating, and wherein the coating is designed to promote endothelial cell growth.

Alternatively or additionally to any of the embodiments above, further comprising a fixation member configured to anchor the medical device to a target tissue site of the left atrial appendage.

Alternatively or additionally to any of the embodiments above, wherein the fixation member includes a plurality of bristles projecting away from an outer surface of the expandable member.

Alternatively or additionally to any of the embodiments above, wherein the fixation member includes a barb projecting away from an outer surface of the expandable member.

Another example medical device for occluding the left atrial appendage includes:

an expandable balloon including an outer surface and an inner expansion cavity;

a plurality of positioning members coupled to the expandable balloon;

a fixation member extending away from the outer surface of the expandable balloon;

wherein the plurality of positioning members are configured to position the medical device within an opening of the left atrial appendage;

wherein the expandable balloon is configured to expand and seal the opening of the left atrial appendage.

Alternatively or additionally to any of the embodiments above, wherein each of the positioning members extends along a longitudinal axis of the balloon from a first end region of the balloon to a second end region of the balloon.

Alternatively or additionally to any of the embodiments above, wherein the second end region of the balloon includes a bottom surface and wherein at least a portion of each of the positioning members is positioned along the bottom surface.

Alternatively or additionally to any of the embodiments above, wherein each of the positioning members is embedded within a wall of the balloon.

Alternatively or additionally to any of the embodiments above, wherein the second end region includes a coating, and wherein the coating is designed to promote endothelial cell growth.

Alternatively or additionally to any of the embodiments above, wherein the fixation member includes a plurality of bristles projecting away from an outer surface of the balloon.

Alternatively or additionally to any of the embodiments above, wherein the fixation member includes a barb projecting away from an outer surface of the balloon.

An example method for sealing the left atrial appendage includes:
  advancing an expandable occluder to a position adjacent the left atrial appendage, wherein the expandable occluder includes:
    an expandable balloon including an inflation cavity;
    a plurality of spine members coupled to the balloon, wherein the spine members are spaced circumferentially around an outer surface of the expandable balloon; and
    a valve member extending at least partially into the inflation cavity; inserting a tubular member into the valve;
  passing an inflation media through the tubular member into the valve; and
  inflating the expandable member to a first position such that the plurality of spine members position the occluder within an opening of the left atrial appendage.

Alternatively or additionally to any of the embodiments above, further comprising:
  inflating the expandable member to a second position in which the expandable member seals against an inner surface of the left atrial appendage.

The above summary of some embodiments is not intended to describe each disclosed embodiment or every implementation of the present disclosure. The Figures, and Detailed Description, which follow, more particularly exemplify these embodiments

BRIEF DESCRIPTION OF THE DRAWINGS

The disclosure may be more completely understood in consideration of the following detailed description of various embodiments in connection with the accompanying drawings, in which.

Figure 1:
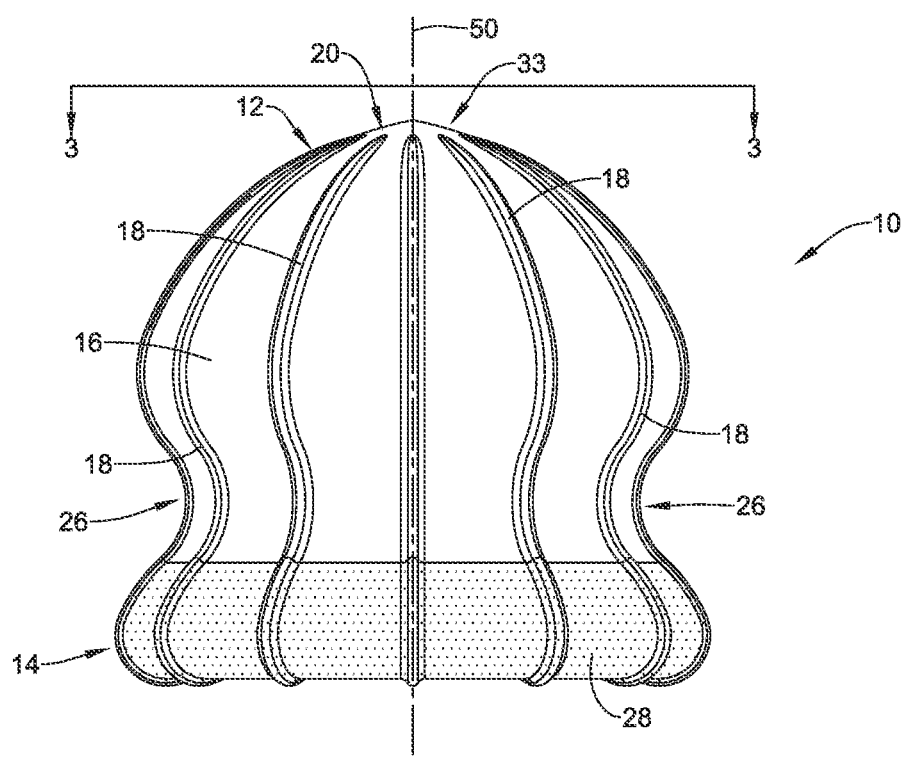
FIG. 1 is a plan view of an example occlusive implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants that close off the left atrial appendage are disclosed herein.

FIG. 1 illustrates an example occlusive implant 10. The occlusive implant 10 may include a first end region 12 and a second end region 14. As will be discussed in greater detail below, the first end region 12 may include the portion of the occlusive implant 10 which extends farthest into a left atrial appendage, while the second end region 14 may include the portion of the occlusive implant 10 which is positioned closer to an opening of the left atrial appendage.

The occlusive implant 10 may include an expandable member 16. The expandable member 16 may also be referred to as an expandable balloon 16. The expandable member 16 may be formed from a highly compliant material (e.g., "inflation material") which permits the expandable member 16 to expand from a first unexpanded (e.g., deflated, collapsed, delivery) configuration to a second expanded (e.g., inflated, delivered) configuration. In some examples, the expandable balloon 16 may be inflated to pressures from about 4 psi to about 200 psi. It can be appreciated that the outer diameter of the implant 10 may be larger in the expanded configuration versus the unexpanded configuration. Example materials used for the inflation material may be hydrogel beads (or other semi-solid materials), saline, etc.

In some examples, the inflatable member may be constructed from silicone or a low-durometer polymer, however, other materials are contemplated. Additionally, the expandable member 16 may be impermeable to blood and/or other fluids, such as water. In some embodiments, the expandable member 16 may include a woven, braided and/or knitted material, a fiber, a sheet-like material, a metallic or polymeric mesh, or other suitable construction. Further, in some embodiments, the expandable member 16 may prevent thrombi (e.g., blood clots, etc.) originating in the left atrial appendage from passing through the occlusive device 10 and into the blood stream. In some embodiments, the occlusive device 10 may promote endothelial growth after implantation, thereby effectively removing the left atrial appendage from the patient's circulatory system. Some suitable, but non-limiting, examples of materials for the occlusive member 10 are discussed below.

Figure 2:
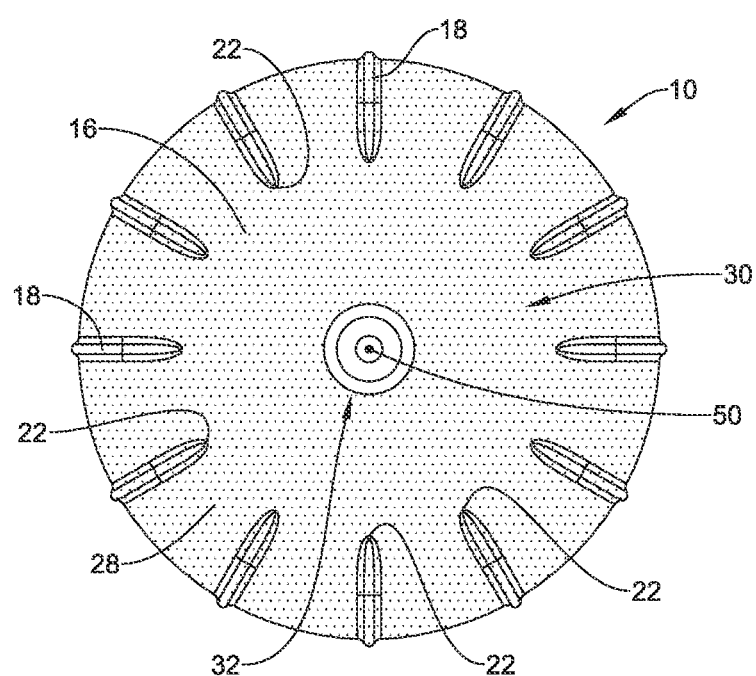
FIG. 2 shows a bottom view of the example occlusive implant shown in FIG. 1.

FIG. 1 further illustrates that occlusive member 10 may include one or more spine members 18 extending along the longitudinal axis 50 of the expandable member 16 from the second end region 14 to the first end region 12. In some examples described herein, the spine members 18 may be described as positioning members 18. Each of the spine members 18 may include a first end 20 and a second end 22 (the second end 22 is shown in FIG. 2). FIG. 1 further illustrates that the each of the individual spine members 18 may be spaced apart from adjacent spine members 18. In other words, the spacing between adjacent spine members 18 may be substantially uniform around the circumference of the expandable member 16. In some examples, the spine members 18 may include one or more materials which are stiffer, higher durometer materials than the material utilized to construct the expandable member 16. Some suitable, but non-limiting, examples of materials for the spine members 18 are discussed below.

Further, it is contemplated that in some instances the spacing between spine members 18 may not be uniform. In some examples, the spacing between adjacent spine members 18 may be variable (e.g., non-uniformly spaced) around the circumference of the expandable member 16. Additionally, it is contemplated that the spine member 18 may form a framework in which the spine members 18 are connected to one another via a series of laterally extending members. A variety of different geometries for example frameworks are contemplated.

As illustrated in FIG. 1, the first end region 12 of the expandable member 16 may extend radially inward to form an apex region 33. Additionally, as shown in FIG. 1, each of the first end portions 20 of each of the spine members 18 may extend inward along the longitudinal axis 50 toward the apex region 33 of the expandable member 16.

Additionally, FIG. 1 illustrates that the occlusive member 10 may include a "nesting region" 26. The nesting region 26 may define a portion of the occlusive member 10 which is configured to nest within an opening of the left atrial appendage (as will be illustrated and described further in FIG. 5). The nesting region 26 may include a portion of the occlusive member 10 which extends radially inward toward the longitudinal axis 50 of the occlusive member 10. Further, the inward curve which defines the nesting region 26 may extend circumferentially around the occlusive member 10. In other words, the inward curvature of the nesting region 26 may resemble a channel or groove which extends around the circumference of the occlusive member 10.

FIG. 1 further illustrates that the second end region 28 of the occlusive member 10 may include a coating 28. The coating 28 may extend around the circumference of the occlusive member 10 (including both the expandable member 16 and the spine members 18). In some examples, the coating 28 may promote cellular growth along the surface thereof. For example, the coating 28 may include elements which promote endothelial growth along the surface thereof. For example, the endothelial growth elements may accelerate the ability for endothelial cellular tissue to form a seal across an opening of the left atrial appendage. In other examples, the coating 28 may include a polymer mesh (e.g., PET mesh), a woven, braided and/or knitted material, a fiber, a sheet-like material, a metallic or polymeric mesh, or other similar materials which may be coupled to the outer surface of the expandable member 16.

FIG. 2 illustrates a bottom view of the occlusive device described in FIG. 1. FIG. 2 illustrates that the occlusive device may include a bottom surface 30. As discussed above, the second end regions 22 of the spine members 18 may "wrap" along (e.g., around) the second end region 14 (shown in FIG. 1) and terminate along the bottom surface 30.

FIG. 2 further shows twelve spine members 18 positioned circumferentially around the longitudinal axis 50 of the occlusive device 10. However, while FIG. 2 illustrates twelve spine members 18 positioned around the longitudinal axis 50 of the occlusive device 10, it is contemplated that more greater or less than twelve spine members 18 may be utilized for any example occlusive devices 10 contemplated herein. For example, occlusive device 10 may include 1, 2, 3, 4, 5, 6, 7, 8, 9, 10, 11, 12, 13, 14, 15, 16 or more spine members 18 positioned along the occlusive device 10.

As will be described in greater detail below, FIG. 2 further illustrates a valve member 32 positioned in a central region of the bottom surface 30 of the occlusive member 10. The valve 32 may be utilized as an access aperture to insert a secondary medical device (not shown). The secondary medical device may be utilized to inject a fluid material into the expandable member 16. FIG. 2 further illustrates that the coating 28 may be positioned along the bottom surface 30 of the occlusive device 10. The coating 28 may cover all or a portion of the bottom surface 30 of the occlusive device 10.

Figure 3:
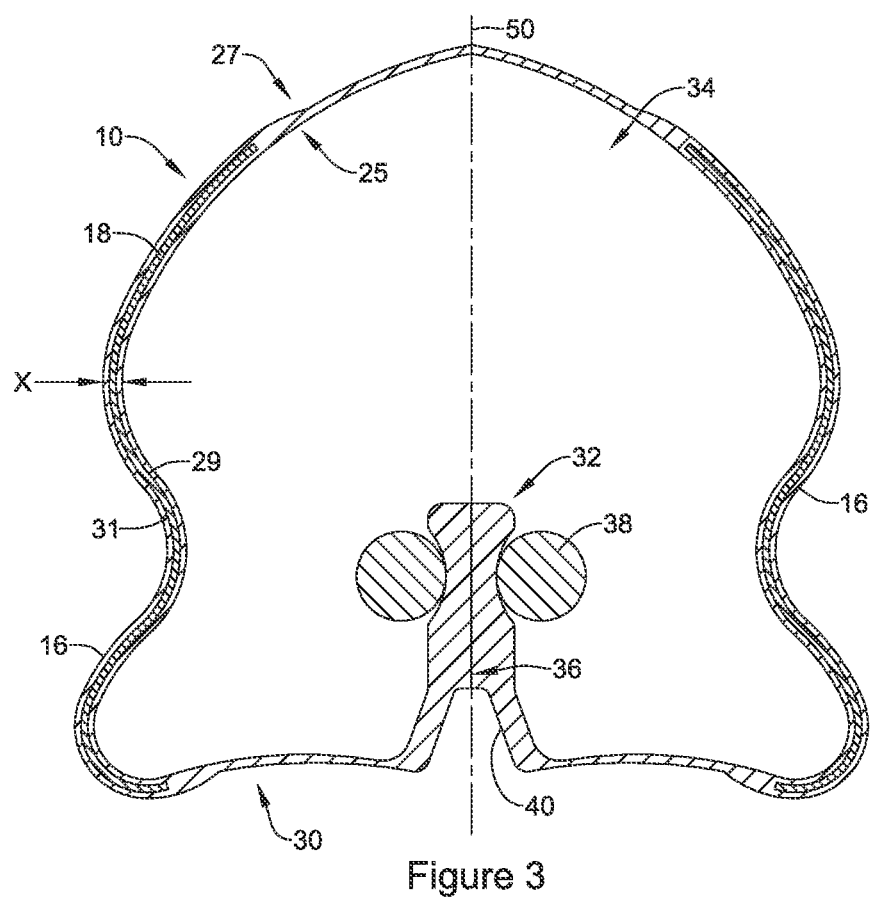
FIG. 3 shows a cross-sectional view along line 3-3 of FIG. 1.

FIG. 3 shows a cross-sectional view along line 3-3 of FIG. 1. FIG. 3 illustrates that the expandable member 16 may include an inner surface 25 and outer surface 27. Additionally, FIG. 3 shows that the expandable member 16 may include a wall thickness "X" defined as the width of the wall between the inner surface 25 and outer surface 27 of the expandable member 16.

FIG. 3 further illustrates that the spine members 18 may be positioned within the wall of the expandable member 16. FIG. 3 illustrates that each of the spine members 18 may include an inwardly-facing surface 29 and an outwardly-facing surface 31. The inner surface 29 of each of the spine members 18 may be positioned radially outward of the inner surface 25 of the expandable member 16. Further, the outer surface 31 of each of the spine members 18 may be positioned radially inward of the outer surface 27 of the occlusive member 10. In other words, each of the spine members 18 be embedded (e.g., encased, surrounded, etc.) within the wall of the expandable member 16. However, this is not intended to be limiting. Rather, it can be appreciated that in some examples, a portion of one or more of the spine members 18 may extend radially away from the outer surface 27 of the expandable member 16. For example, in some instances a portion of the outer surface 31 of one or more of the spine members 18 may be free from the expandable member 16.

FIG. 3 further illustrates that the expandable member 16 may include an inner cavity 34. Inner cavity 34 may be described as a chamber in which in an inflation media (e.g., hydrogel beads, semi-solid materials, saline or other suitable liquids, gases, etc.) may be injected (via valve 32, for example) in order to expand the expandable member 16. As will be described in greater detail below, as an inflation media is inserted into the expandable member 16, the inner cavity 34 may expand, thereby permitting the expandable member 16 to seal against the tissue walls defining an opening in the left atrial appendage.

As stated above, inflation of the inner cavity 34 may be accomplished by inserting inflation media through the valve 32. As shown in FIG. 2, the valve 32 may be formed from the same material that forms the wall of the expandable member 16. In other words, the valve 32 may be an extension of the wall of the expandable member 16. Additionally, as illustrated in FIG. 3, the valve 32 may be positioned within the inner cavity 34. For example, FIG. 3 illustrates that the valve 32 may extend (e.g., project) into the inner cavity 34 from the bottom surface 30.

The valve 32 may include an inflation lumen 36 which may be designed to allow a secondary medical device to be inserted therethrough. As shown in FIG. 3, the inflation lumen 36 may be aligned with the longitudinal axis 50 of the occlusive member 10. FIG. 3 shows the inflation lumen 36 in a closed configuration such that it would prevent inflation media (not shown in FIG. 3) from passing back through the valve 32. As shown in FIG. 3, in some examples the valve 32 may be maintained in a closed configuration via a torus-shaped mechanical gasket 38. For simplicity purposes, the gasket 38 may be referred to as an "O-ring" in the remaining discussion.

It can be appreciated that the O-ring 38 may be formed from a material (e.g., rubber, elastomer, etc.) which permits it to compress radially inwardly. As shown in FIG. 3, the O-ring 38 may be positioned around the valve 32 such that the O-ring 38 compresses the lumen 36 of valve 32 shut. However, the O-ring 38 must also permit the lumen 36 to open enough for a secondary medical device to be inserted therethrough (for inflation of the expandable member 16 as described above). Therefore, in some examples the O-ring 38 may designed to stretch and allow an inflation device access to the inner chamber 34 while also exerting sufficient radially inward force to maintain the lumen 36 in a closed configuration once the inner chamber 34 has been inflated and after the inflation device (not shown in FIG. 3) is removed from the lumen 36 (inflation of the chamber 34 will be discussed with respect to FIG. 9 and FIG. 10).

As will be discussed in greater detail below, the occlusive member 10 may be coupled to a delivery system in a variety of ways. Further, a component of the delivery system may also function as a secondary medical device utilized to inflate the expandable member 16. FIG. 3 illustrates an attachment region 40 which may be utilized to attach the delivery system to the occlusive member 10. Attachment region 40 may be include a variety of features which permit attachment to a delivery system. For example, attachment region 40 may include threads which mate with a threaded region on a delivery catheter (not shown in FIG. 3). In other examples, the attachment region 40 may be designed such that it forms a "press-fit" with a distal end region of a delivery catheter. Other methods of attaching the occlusive device 10 to the delivery catheter may include a ratcheting mechanism, break-away mechanisms, detent lock, spring lock, single-piece coupling, two-piece coupling, or combinations thereof.

Figure 4:
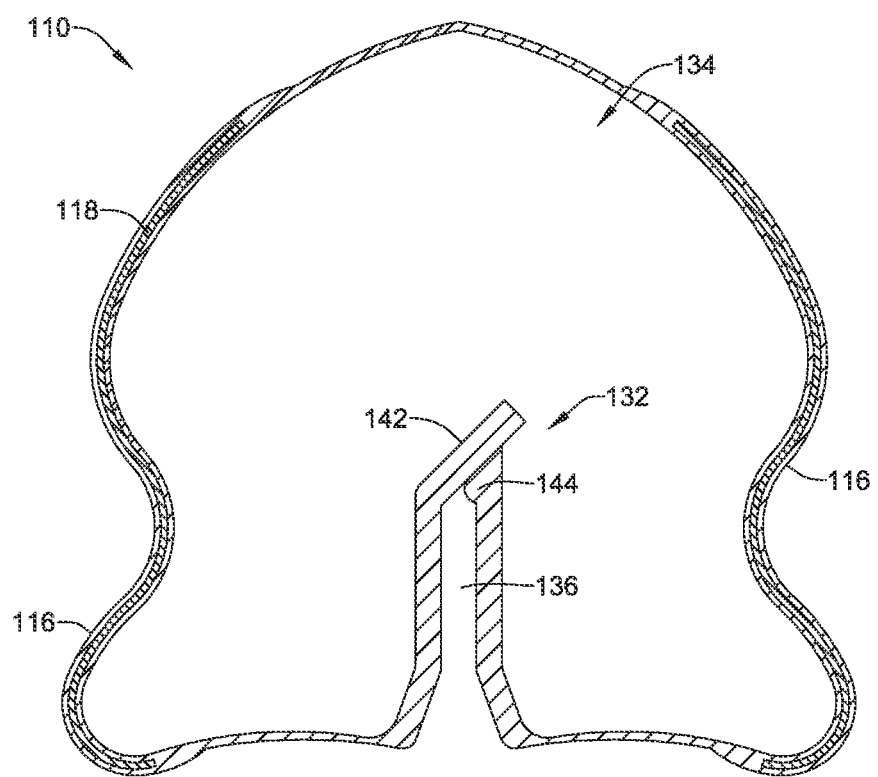
FIG. 4 shows a cross-sectional view of another example occlusive implant.

FIG. 4 illustrates a cross-sectional view of another example occlusive device 110. The occlusive device 110 may be similar in form and function as the occlusive device 10. For example, the occlusive device 110 may include an expandable member 116 and one or more spine members 118 coupled thereto. Additionally, the occlusive device 110 may include a valve 132. The valve 132 illustrated in FIG. 4 may function in a similar manner as the valve 32 described above. However, as illustrated in FIG. 4, the valve 132 may include a flap 142 configured to mate with a support member 144. It can be appreciated from FIG. 4 that in some instances the flap 142 and the support member 144 may resemble a one-way valve system whereby the flap 142 is designed to permit inflation media (or an inflation device) to access an inner chamber 134 while preventing inflation media from exiting the inner chamber 134 once the expandable member 116 has been inflated to a sufficient extent. In other words, the flap 142 may be designed to pivot counter-clockwise, thereby allowing lumen 136 to access the inner chamber 134 of the expandable member 116.

Figure 5:
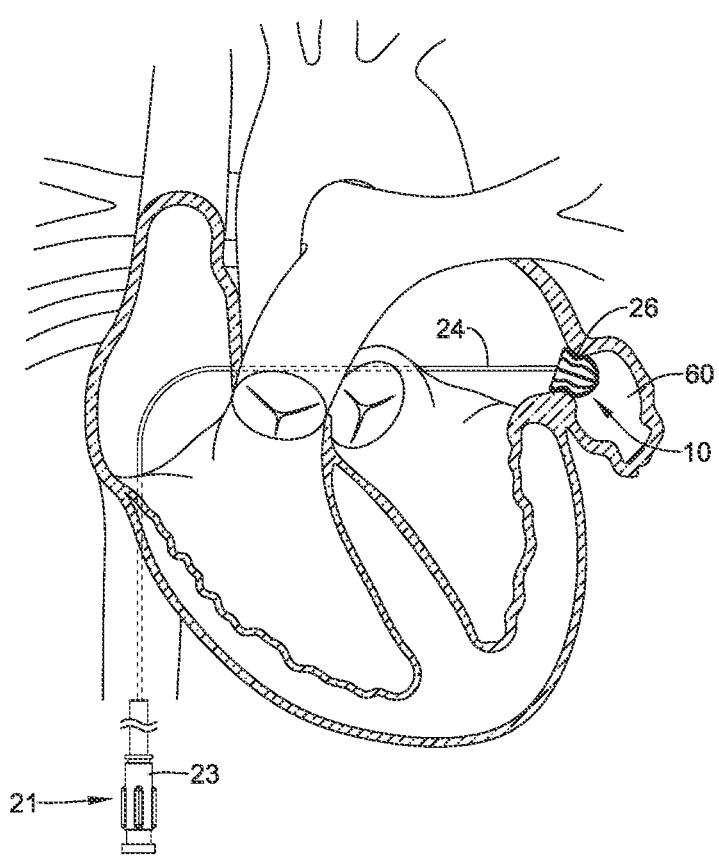
FIG. 5 shows an example occlusive implant positioned in an opening of the left atrial appendage.

FIG. 5 illustrates that the occlusive implant 10 may be inserted and advanced through a body lumen via an occlusive implant delivery system 21. FIG. 5 further illustrates the occlusive implant 10 positioned within the left atrial appendage 60. As discussed above, in some instances the occlusive implant 10 may be positioned within the left atrial appendage such that the nesting region 26 is anchored within a portion of the left atrial appendage 60.

In some instances, an occlusive implant delivery system 21 may include a delivery catheter 24 which is guided toward the left atrium via various chambers and lumens of the heart (e.g., the inferior vena cava, the superior vena cava, the right atrium, etc.) to a position adjacent the left atrial appendage 60. The delivery system 21 may include a hub member 23 coupled to a proximal region of the delivery catheter 24. The hub member 23 may be manipulated by a clinician to direct the distal end region of the delivery catheter 24 to a position adjacent the left atrial appendage 60. As discussed above, a proximal end of the occlusive device 10 may be configured to releasably attach, join, couple, engage, or otherwise connect to the distal end of the delivery catheter 24. In some embodiments, an end region of the occlusive device 10 may include a threaded insert coupled thereto. In some embodiments, the threaded insert may be configured to and/or adapted to couple with, join to, mate with, or otherwise engage a threaded member disposed at the distal end of the delivery catheter 24. Other means of releasably coupling and/or engaging the proximal end of the occlusive device 10 to the distal end of the delivery catheter are also contemplated. Further, in some examples the delivery catheter 24 may include an inflation lumen (not show) designed to permit inflation media to pass into the occlusive device 10 (as described above). For example, in some examples, the distal end of the delivery catheter 24 may include a needle designed to be inserted through the valve 32 (discussed in FIG. 3).

Figure 6:
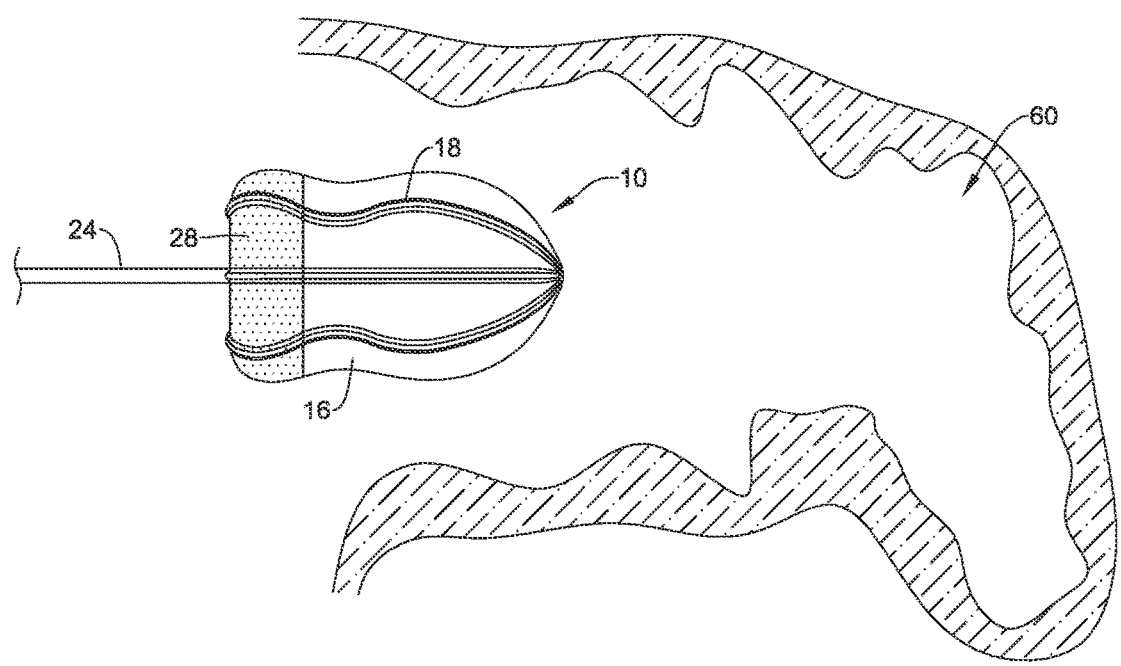
FIGS. 6-10 illustrate an example occlusive implant being positioned within an opening of the left atrial appendage.
Figure 7:
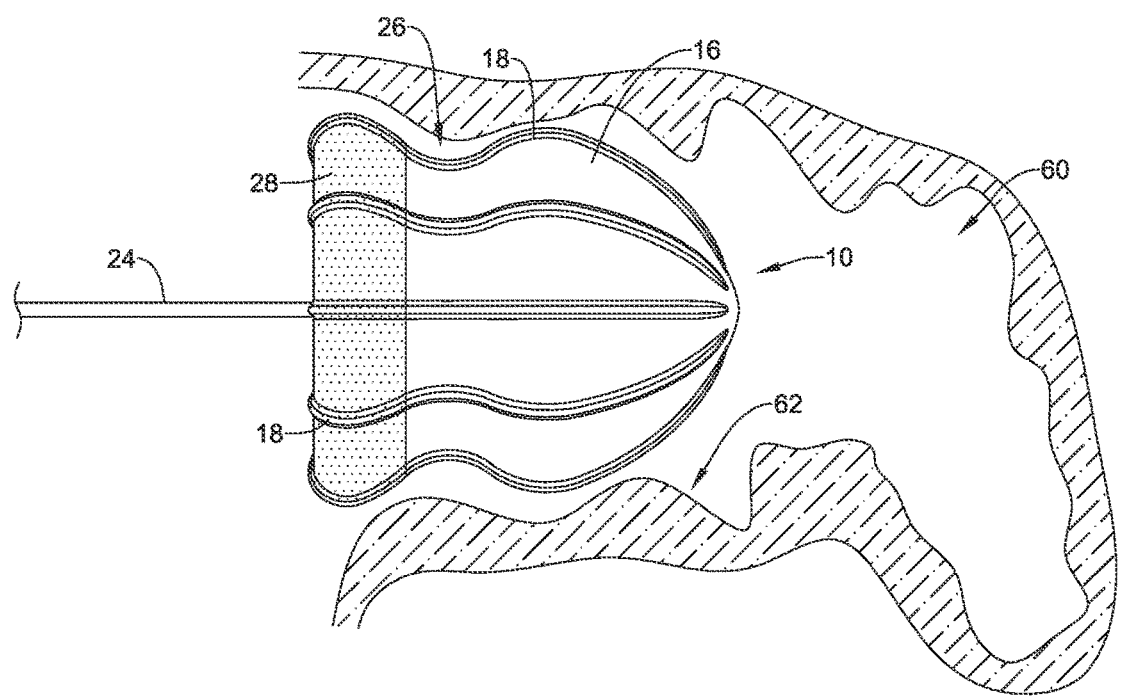
Figure 8:
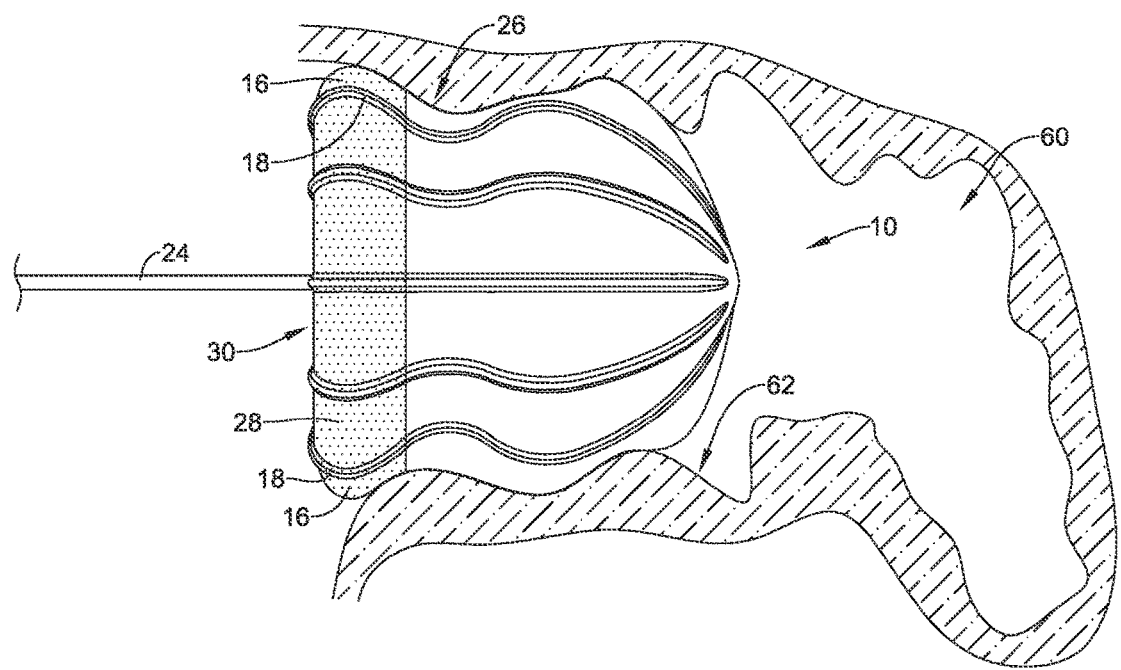

FIGS. 6-8 illustrate the example occlusive device 10 (described above) being positioned and deployed in an opening of the left atrial appendage 60. As discussed above, in some examples, the occlusive device 10 may be configured to shift between a collapsed configuration and an expanded configuration. For example, in some instances, the occlusive implant may be in a collapsed configuration during delivery via an occlusive device delivery system, whereby the occlusive device expands to an expanded configuration once deployed from the occlusion implant delivery system.

FIG. 6 shows the occlusive device 10 including an expandable member 16, a plurality of spine members 18 and a cellular-growth promoting coating 28 (as described above). Further, FIG. 6 illustrates that the occlusive member 10 may be detachably coupled to a delivery catheter 24. The occlusive member 10 shown in FIG. 6 may be described as being in a deflated or delivery configuration. In other words, the expandable member 16 may not contain any inflation media within its inner cavity. It can be appreciated that it may be desirable to maintain the occlusive member 10 in a collapsed configuration when delivering the occlusive member 10 to the target site (e.g., an opening in the left atrial appendage 60). A collapsed configuration may permit the occlusive member 10 to more easily track through tortuous vasculature as a clinician directs the device to the target site.

FIG. 7 illustrates an example first stage in deployment of the occlusive member 10. FIG. 7 shows the expandable member 16 expanded to a larger diameter as compared with the non-expanded configuration illustrated in FIG. 6. It can be appreciated that inflation media has been injected into the inner chamber of the expandable member 16, whereby the inflation media shifts the expandable member from the deflated configuration (shown in FIG. 6) to the partially-inflated configuration shown in FIG. 7.

Additionally, FIG. 7 illustrates that as the expandable member 16 inflates radially outward, the spine members 18 approach and may contact the inner surface 62 (e.g., the tissue wall) of the left atrial appendage 60. It can be appreciated that as the spine members 18 (which are circumferentially spaced around the expandable member 16) begin to contact the inner surface 62 of the left atrial appendage 60, they may center and maintain the occlusive device 10 within the opening of the left atrial appendage 60. Additionally, as the spine members 18 contact the inner surface 62 of the atrial appendage 60 they may reduce the likelihood that occlusive device 10 will shift its position within the left atrial appendage 60. Additionally, when aligned properly, the nesting region 26 of the occlusive member 10 may nest within a portion of the wall of the left atrial appendage 60, thereby furthering reducing the likelihood that the occlusive member 10 will shift its position while in the partially deflated state shown in FIG. 7.

FIG. 8 illustrates the occlusive member 10 in a fully inflated state. Additionally, FIG. 8 illustrates that the expandable member 16 may be compliant and, therefore, substantially conform to and/or be in sealing engagement with the shape and/or geometry of a lateral wall 62 of a left atrial appendage 60 while in the inflated (e.g., expanded) configuration. In some embodiments, the occlusive device 10 may expand to a size, extent, or shape different from a maximum unconstrained extent, as determined by the surrounding tissue and/or lateral wall 62 of the left atrial appendage 60.

As can be appreciated from FIG. 8, continued inflation of the expandable member 16 beyond the partially inflated state shown in FIG. 7 may permit the expandable member 16 to expand and conform to the specific geometry of the inner surface 62 of the left atrial appendage 60. In other words, as inflation media is added to the expandable member 16, the expandable member 16 may fill and/or seal gaps in the opening of the left atrial appendage 60 which may not have been sealed while the occlusive device 10 was partially inflated (as shown in FIG. 7). It can be appreciated that the flexible material used to construct the expandable member 16 may stretch, conform and directly oppose the folded curvature of the inner surface 62 of the left atrial appendage 60. For example, FIG. 8 shows the expandable member 16 expanded such that the expandable member 16 is contacting the curved inner surface 62 of the left atrial appendage 60, thereby sealing the opening of the left atrial appendage 60. Additionally, FIG. 8 illustrates the nesting region 26 of the occlusive member seated within a portion of the inner surface 62 of the left atrial appendage 60.

It can further be appreciated from FIG. 8 that the bottom surface 30 of the occlusive device is positioned such that it is facing the left atrium of the heart. As discussed above, the bottom surface 30 of the occlusive device 10 may include the cellular-growth promoting coating 28. Accordingly, the cellular-growth promoting coating 28 is positioned to promote the growth of endothelial cellular tissue across the bottom surface 30 of the occlusive implant 10, thereby effectively sealing the left atrial appendage 60.

Figure 9:
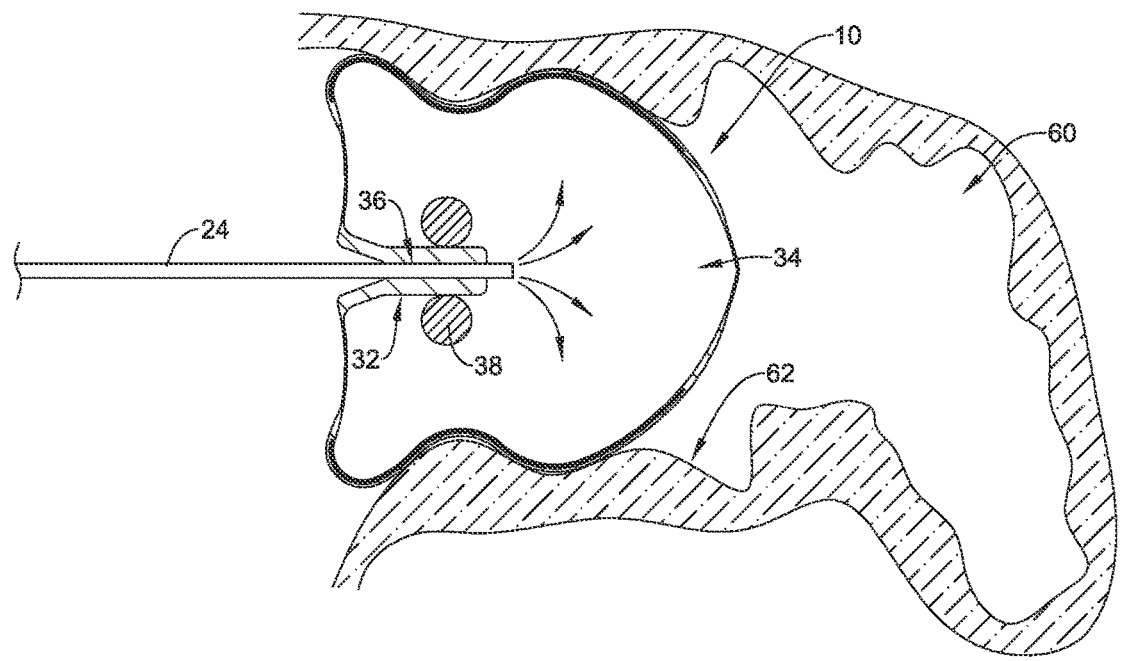
Figure 10:
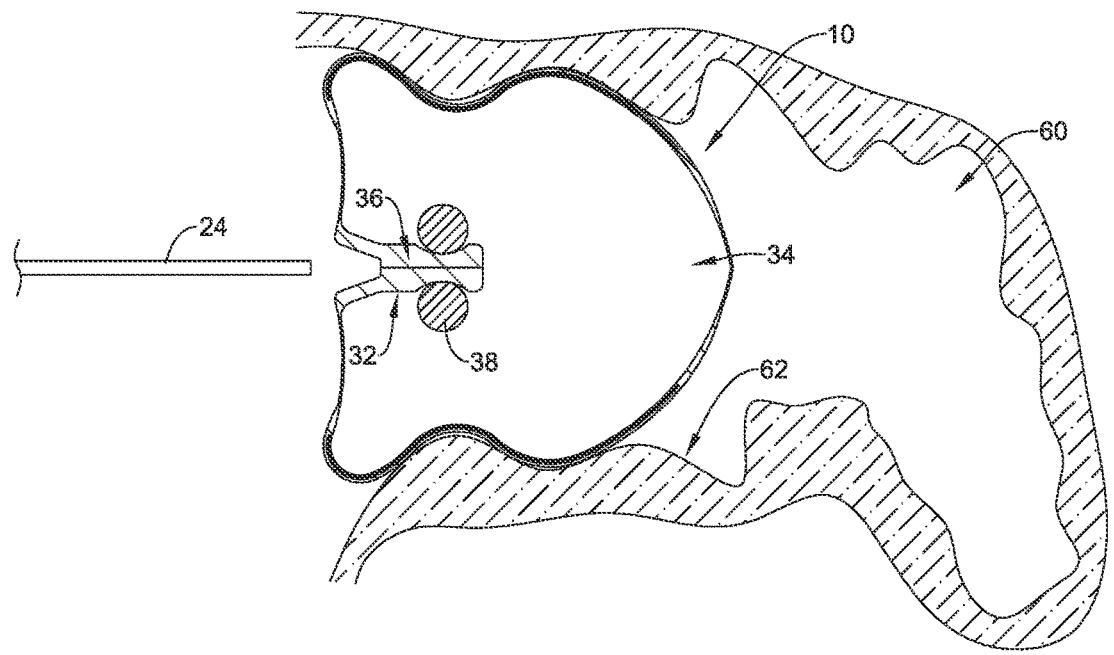

FIG. 9 and FIG. 10 show cross-sectional views of the occlusive device 10 being inflated from a partially-inflated state (shown in FIG. 7) to a fully inflated state (shown in FIG. 8.) whereby the expandable member 16 fully opposes the inner surface 62 of the left atrial appendage 60. FIG. 9 further illustrates a delivery catheter 24 (described above in some examples as a secondary medical device) having been advanced through the lumen 36 of the valve 32. As described above, the O-ring 38 has expanded radially outward to permit the distal end region of the delivery catheter 24 to be advanced through the valve lumen 36 and into the inner chamber 34 of the expandable member 16. Once positioned within the inner chamber 34, the inflation media (depicted by the arrows in FIG. 9) may be injected into the inner chamber 34, thereby expanding the occlusive device 10 as described above.

FIG. 10 shows the occlusive device 10 deployed along the inner surface 62 of the left atrial appendage 60. Further, FIG. 10 illustrates the delivery catheter 24 described above in FIG. 9 having been removed from the inflation lumen 36 of the valve 32. It can be appreciated from FIG. 10 that the O-ring 38 has been compressed radially inward such that it has closed the lumen 36. It can be further appreciated that the O-ring 38 may designed to exert sufficient radially inward force along the valve 36 to prevent the inflation media from passing back through the valve 32 (which may partially collapse the occlusive device 10).

Figure 11:
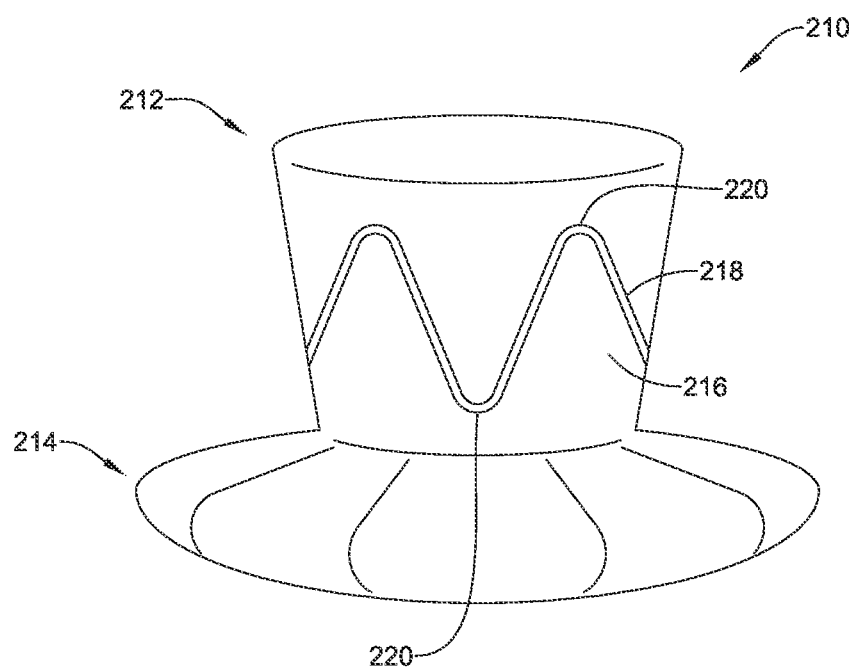
FIG. 11 illustrates another example occlusive implant.

FIG. 11 illustrates another example occlusive device 210. Occlusive device 210 may be similar in form and function to other occlusive devices described above (e.g., occlusive device 10). Occlusive device 210 may include an expandable member 216 including a first end region 212 and a second end region 214. The expandable member 216 may be similar in form and function to the expandable member 16 described above.

Occlusive device 210 may include a positioning member 218. The positioning member 218 may function similarly to the spine members 18 described above. However, as illustrated in FIG. 11, the spine member 218 may extend around the circumference of the expandable member 216. Further, the spine member 218 may include a plurality of curved portions 220. In some examples, the spine member 218 may provide additional radial support for the occlusive device 210. Additionally, in some examples, the expandable member 216 may expand in the radial direction a greater distance than the spine member 218. The ability for the expandable member 216 to expand farther (in the radial direction) than the spine member 218 may permit the expandable member 218 to conform to the irregularly-shaped folds and curved surfaces of a left atrial appendage.

While not illustrated in FIG. 11, it is contemplated that the occlusive device 210 may include more than one expandable member 216. For example, the first end region 212 may include a first expandable member and the second end region 214 may include a second expandable member which operates independently of the first expandable member.

Figure 12:
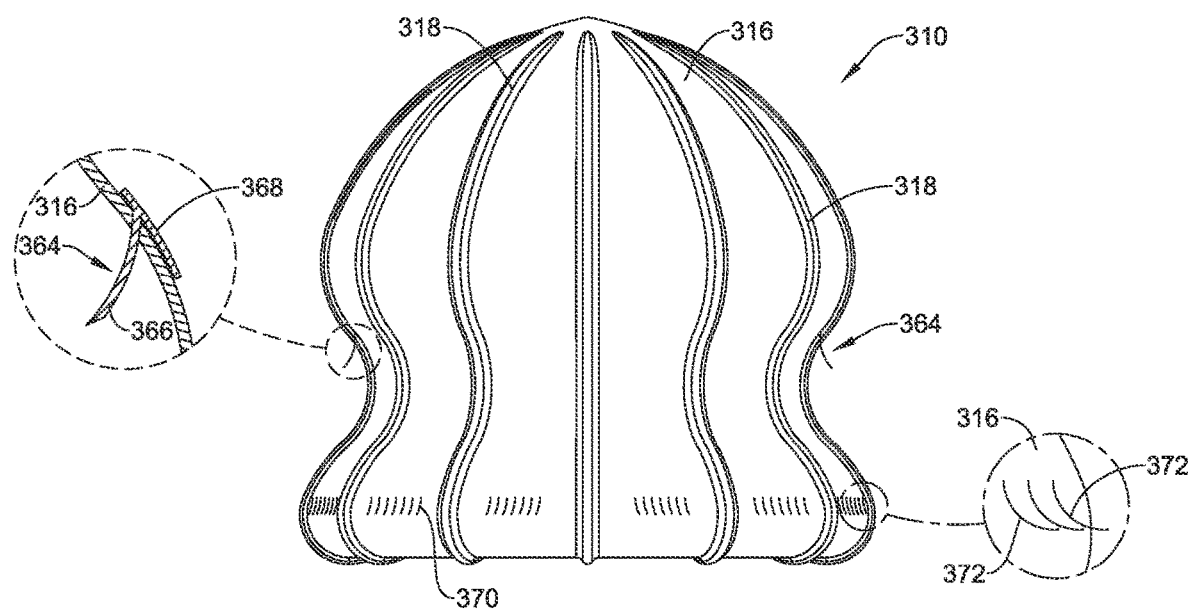
FIG. 12 illustrates another example occlusive implant including fixation members.

FIG. 12 illustrates another example occlusive device 310. Occlusive device 310 may be similar in form and function to other occlusive devices described above (e.g., occlusive device 10). Occlusive device 310 may include an expandable member 316 and a plurality of spine members 318 coupled thereto. Further, FIG. 12 illustrates that the occlusive device 310 may include a plurality of anchor members 364 disposed along the expandable member 316. It can be appreciated that in some examples the occlusive device 310 may be affixed to a left atrial appendage by one or more anchoring members 364. For example, when the occlusive device 310 is positioned adjacent the inner surface of the left atrial appendage (as shown in FIG. 8), the anchor members 364 may extend radially outward from the expandable member 316 and contact the tissue of the left atrial appendage thereby anchoring the occlusive implant 310 in a fixed position.

In some embodiments, at least some of the anchor members 364 may include a base 368 and a tip portion 366 projecting radially away from the base 368, as shown in FIG. 12. For example, the detailed view of FIG. 12 illustrates the base 368 of anchor member 364 positioned along an inner surface of the expandable member 316. Further, FIG. 12 illustrates the tip portion 366 extending through the wall of the expandable member 316 such that it extends away from the expandable member 316. In other examples, it is contemplated that the base 368 of the anchor members 364 may be bonded directly to the outer surface of the expandable member 316. Further, in other examples it is contemplated that the base 368 of the anchor members 364 may be bonded directly to a portion of the spine members 318.

FIG. 12 illustrates two anchor members 364 positioned along the occlusive device 310. However, this is not intended to be limiting. Rather, the occlusive device 310 may include 1, 2, 3, 4, 5, 6, 7, 8, 9, 10, 11, 12, 13, 14, 15, 16 or more anchor members 364. Additionally, it is contemplated that an anchor member 364 may be positioned along a spine member 318. However, this is not intended to be limiting. Rather, it is contemplated that more than one anchor members 364 may be attached to a single spine member 318. For example, a single spine member 318 may include 1, 2, 3, 4, 5, 6, or more anchor members 364 attached thereto.

Additionally or alternatively, the occlusive device 310 may include fixation elements 370 disposed along the outer surface of expandable member 316 and/or the spine members 318. Fixation elements 370 may include one or more individual bristles 372 positioned adjacent one another. In some examples, the bristles made be formed from a metal (e.g., stainless steel), a polymer (e.g., polyester, etc.) or combinations thereof. As illustrated in the detailed view in FIG. 12, the bristles may extend radially away from the outer surface of the expandable member 316. Further, a plurality of the fixation elements 370 may be positioned in a variety of locations along the occlusive member 310. FIG. 12 illustrates six fixation elements 370 positioned along the occlusive device 310. However, this is not intended to be limiting. Rather, the occlusive device 310 may include 1, 2, 3, 4, 5, 6, 7, 8 or more fixation elements 370. The fixation elements 370 may improve the ability of the occlusive device 310 to grip and maintain its position when positioned within the left atrial appendage.

Figure 13:
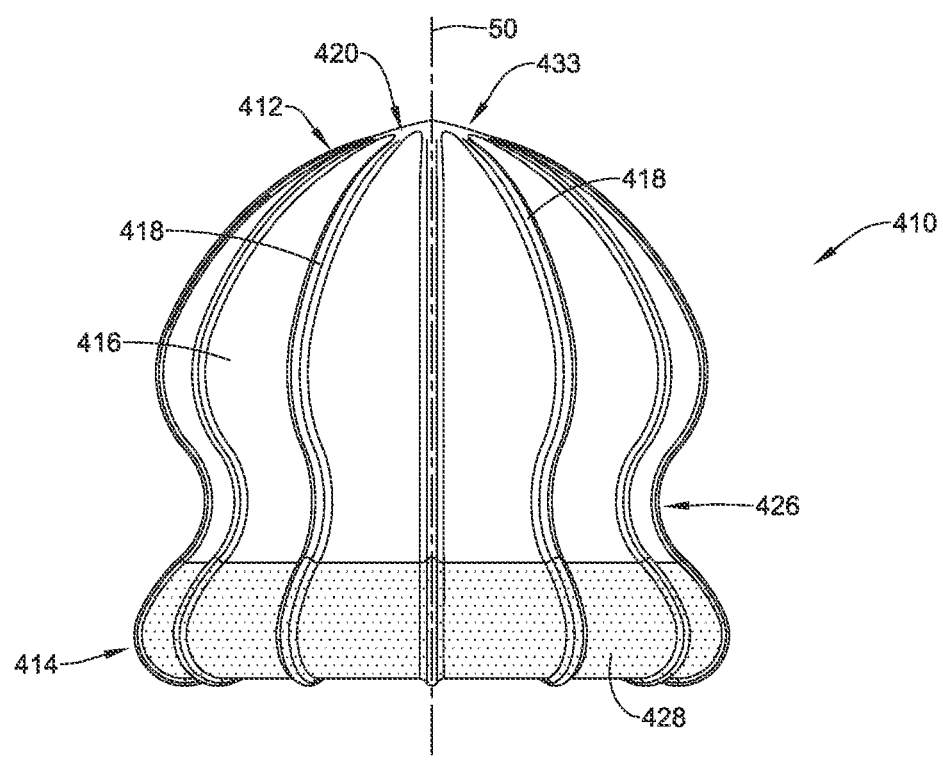
FIG. 13 illustrates another example occlusive implant.

FIG. 13 illustrates another example occlusive device 410. The occlusive device 410 may be similar in form and function as the occlusive device 10 described above. For example, the occlusive device 410 may include an expandable member 416 and one or more spine members 418 coupled thereto. The expandable member 416 may be formed from a highly compliant material (e.g., "inflation material") which permits the expandable member 416 to expand from a first unexpanded (e.g., deflated, collapsed) configuration to a second expanded (e.g., inflated) configuration (as described above with respect to the occlusive device 10).

As discussed above, FIG. 13 illustrates that occlusive member 410 may include one or more spine members 418 extending along the longitudinal axis 50 of the expandable member 416 from the second end region 414 to the first end region 412. In some examples described herein, the spine members 418 may be described as positioning members 418. Each of the spine members 418 may include a first end 420 disposed along the first end region 412 and a second end (not shown in FIG. 13) disposed along the bottom surface (not shown in FIG. 13) of the occlusive member 410. FIG. 13 further illustrates that the each of the individual spine members 418 may be spaced apart from adjacent spine members 418. In other words, the spacing between adjacent spine members 418 may be substantially uniform around the circumference of the expandable member 416. In some examples, the spine members 418 may include one or more materials which are stiffer, higher durometer materials than the material for which the expandable member 416 is constructed. Some suitable, but non-limiting, examples of materials for the spine members 418 are discussed below.

As illustrated in FIG. 13, the first end region 412 (including spine members 418) of the expandable member 416 may extend radially inward to form an apex region 433. Additionally, as shown in FIG. 13, each of the first end portions 420 of each of the spine members 418 may extend inward along the longitudinal axis 50 toward the apex region 433 whereby each of the first end portions 420 of the spine members 418 may combine (e.g., engage, affix, attach, etc.) with one another to form the apex region 433. It can be appreciated that combining the first end portions 420 of each of the spine members to one another may limit the elongation of the occlusive implant 410 along the longitudinal axis 50 when the occlusive implant 410 shifts from an unexpanded configuration to an expanded configuration (as described above). In other words, when the first end portions 420 of each of the spine members 418 are attached to one another, they may work together to resist the longitudinal elongation imparted by the expandable member 416 along the longitudinal axis 50 of the occlusive implant 410 when the occlusive implant 410 shifts from an unexpanded configuration to an expanded configuration (as described above).

FIG. 13 further illustrates that the second end region 414 of the occlusive member 410 may include a coating 428. The coating 428 may extend around the circumference of the occlusive member 410 (including both the expandable member 416 and the spine members 418). In some examples, the coating 428 may promote cellular growth along the surface thereof. For example, the coating 428 may include elements which promote endothelial growth along the surface thereof. For example, the endothelial growth elements may accelerate the ability for endothelial cellular tissue to form a seal across an opening of the left atrial appendage. In other examples, the coating 428 may include a polymer mesh (e.g., PET mesh) or similar covering which may be attached to the outer surface of the occlusive member 410.

Additionally, FIG. 13 illustrates that the occlusive member 410 may include a "nesting region" 426. The nesting region 426 may define a portion of the occlusive member 410 which is configured to nest within an opening of the left atrial appendage. The nesting region 426 may include a portion of the occlusive member 10 which extends radially inward toward the longitudinal axis 50 of the occlusive member 410. Further, the inward curve which defines the nesting region 426 may extend circumferentially around the occlusive member 410. In other words, the inward curvature of the nesting region 426 may resemble a channel or groove which extends around the circumference of the occlusive member 410.

Figure 14:
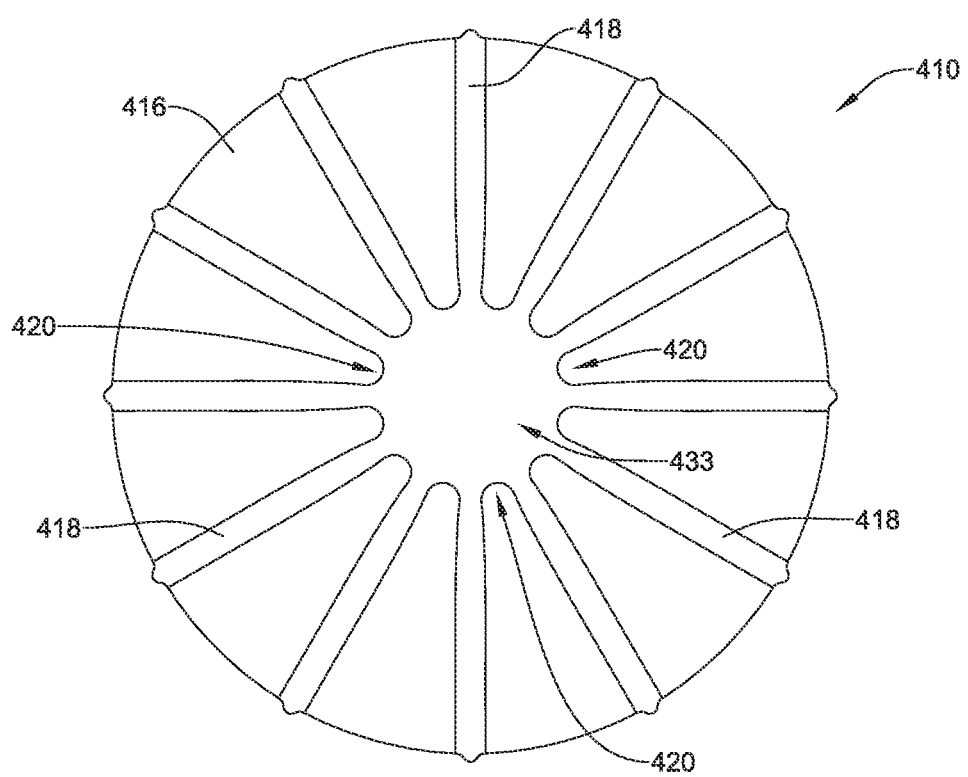
FIG. 14 illustrates a top view of the occlusive implant shown in FIG. 13.

FIG. 14 shows a top view of the occlusive member 410 shown in FIG. 13. Specifically, FIG. 14 illustrates the first end portions 420 of the spine members 418 extending radially inward to form the apex region 433. As discussed above, while FIG. 14 illustrates the spine members 418 being evenly spaced from one another, it can be appreciated that the spine members 418 may be spaced at unequal intervals from one another.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni-Co-Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device for occluding the left atrial appendage, comprising:

an expandable member defining a first end region with a distal end, a second end region and an inflation cavity;

a plurality of spine members coupled to the expandable member, the plurality of spine members spaced circumferentially around an outer surface of the expandable member, the spine members extend distally from the second region to the first region, and the spine members terminate prior to reaching the distal end; and a valve member extending at least partially into the inflation cavity;

wherein the expandable member extends distal of the plurality of spine members;

wherein the plurality of spine members are configured to position the medical device within an opening of the left atrial appendage;

wherein the expandable member is configured to expand and seal the opening of the left atrial appendage.

2. The medical device of claim 1, wherein the second end region includes a bottom surface and wherein at least a portion of each of the spine members is positioned along the bottom surface.

3. The medical device of claim 2, wherein the expandable member includes a curved portion extending radially inward toward the longitudinal axis, and wherein the curved portion is configured to nest with the opening of the left atrial appendage.

4. The medical device of claim 1, wherein a portion of each of the spine members is positioned along an outer surface of the expandable member.

5. The medical device of claim 1, wherein the first end region of the expandable member extends toward a longitudinal axis of the medical device to form an apex.

6. The medical device of claim 1, wherein the second end region includes a coating, and wherein the coating is designed to promote endothelial cell growth.

7. The medical device of claim 1, further comprising a fixation member configured to anchor the medical device to a target tissue site of the left atrial appendage.

8. The medical device of claim 7, wherein the fixation member includes a plurality of bristles projecting away from an outer surface of the expandable member.

9. The medical device of claim 7, wherein the fixation member includes a barb projecting away from an outer surface of the expandable member.

* * * * *